United States Patent
Dykstra

(10) Patent No.: US 6,465,446 B1
(45) Date of Patent: Oct. 15, 2002

(54) TREATMENT OF DERMATITIS BY THE TOPICAL APPLICATION OF Δ5-ANDROSTENE-3β-OL-7,17 DIONE AND METABOLIZABLE PRECURSORS THEREOF

(76) Inventor: John C. Dykstra, 6844 Jeremy Ct., Eden Prairie, MN (US) 55346

( * ) Notice: Subject to any disclaimer, the term of this patent is extended or adjusted under 35 U.S.C. 154(b) by 0 days.

(21) Appl. No.: 09/805,024

(22) Filed: Mar. 12, 2001

(51) Int. Cl.$^7$ ................................................ A61K 31/56
(52) U.S. Cl. ...................... 514/178; 514/177; 514/169; 514/170
(58) Field of Search ................................ 514/177, 178, 514/169, 170

(56) References Cited

U.S. PATENT DOCUMENTS

| | | | |
|---|---|---|---|
| 5,292,730 A | 3/1994 | Lardy | 514/171 |
| 5,296,481 A | 3/1994 | Partridge et al. | 514/178 |
| 5,424,463 A | 6/1995 | Lardy et al. | 552/637 |
| 5,506,223 A | 4/1996 | Lardy et al. | 514/178 |
| 5,585,371 A | 12/1996 | Lardy | 514/171 |
| 5,641,766 A * | 6/1997 | Lardy | 514/171 |
| 5,707,983 A | 1/1998 | Lardy | 514/177 |
| 5,807,848 A | 9/1998 | Lardy | 514/171 |
| 5,885,977 A | 3/1999 | Pauza et al. | 514/171 |
| 5,972,917 A * | 10/1999 | Bishop et al. | 514/167 |
| 6,153,606 A | 11/2000 | Lardy et al. | 514/177 |

FOREIGN PATENT DOCUMENTS

| | | | | |
|---|---|---|---|---|
| WO | WO 99/25192 | 5/1999 | ........... | A01N/45/00 |
| WO | WO 99/25333 | 5/1999 | ........... | A61K/31/33 |

OTHER PUBLICATIONS

Malaviya et al., Journal of Molecular Medicine, (Aug. 1998) 76 (9) 617–23.*
de Weck A L., Federation Proceedings, (Apr. 1977) 36 (5) 1742–7.*
Pike et al. Nutrition An Integrated Approach (3rd ED) (1984), p. 553.*
U.S. patent application Ser. No. 09/641,193, Zenk, filed Aug. 2000.
U.S. patent application Ser. No. 09/665,640, Zenk et al., filed Sep. 2000.
U.S. patent application Ser. No. 60/250,227, Zenk et al., filed Nov. 2000.
"Grapeseed Palma Christi Lotion; DHEA Crème Moisturizer with Antioxidants; Citronella Aura Glow Massage Formula; Russian Whit Oil Manufacturer: Heritage Store Category: Skin Care," *Product Alert*, May 12, 1997 (Abstract).
"Sweet Dreams Melatonin Night Cream; DHEA Day Cream; Manufacturer: Emerald Pharmaceuticals Catagory: Skin Care," *Product Alert*, May 12, 1997 (Abstract).
Berliner, David L., "Biotransformation of Steroids by the Skin," *Advances in Biology of Skin, vol. XII, Pharmacology and the Skin*, p. 357–365, 1969.
Berliner, David L. et al., "The Formation of Water Soluble Steroids by Human Skin," *The Journal of Investigative Dermatology*, vol. 50, No. 3, p. 220–224, 1968.
Faredin, I. et al., "The Metabolism of [4–$^{14}$C]5–Androstene–3β,17β–Diol by Normal Human Skin in Vitro," *Acta Medica Academiae Scientiarum Hungaricae*, vol. 32, p. 139–152, 1975.
Faredin, I. et al., "The in Vitro Metabolism of Dehydroepiandrosterone in the Human Skin," *Acta Medica Academiae Scientiarum Hungaricae*, vol. 23, p. 169–180, 1967.
Frost, Phillip,et al., "Metabolism of Estradiol–17β and Estrone in Human Skin," *The Journal of Investigative Dermatology*, vol. 46, No. 6, pp. 584–585, 1966.
Gallegos, A.J., "Transformation and Conjugation of Dehydroepiandrosterone by Human Skin," *The Journal of Clinical Endocrinology and Metabolism*, vol. 27, No. 7, p. 1214–1218, Jul. 1967.
Klein, A. et al., "Effect of a non–viral fraction of acquired immunodeficiency syndrome plasma on the vulnerability of lymphocytes to cortisol," *Journal of Endocrinology*, vol. 112, No. 2, p. 259–264, Feb. 1987.
Malkinson, Frederick D. et al., "In Vitro Studies of Adrenal Steriod Metabolism in the Skin," *The Journal of Investigative Dermatology*, p. 101–107.
Xu, Pengjin et al., "Characterization of Physico–Chemical Properties and Skin Permeability of Dehydroepiandrosterone," *Pharmaceutical Research*, vol. 12, No. 9, p. S–273, Sep. 1995 (Supplement).

* cited by examiner

*Primary Examiner*—Russell Travers
*Assistant Examiner*—S. Jiang
(74) *Attorney, Agent, or Firm*—Michael S. Sherrill

(57) ABSTRACT

Dermatitis can be treated by the administration of Δ5-androstene-3β-ol-7,17 dione and metabolizable precursors thereof, such as Δ5-androstene-3β-acetoxy-7,17 dione, to the skin.

15 Claims, No Drawings

TREATMENT OF DERMATITIS BY THE TOPICAL APPLICATION OF Δ5-ANDROSTENE-3β-OL-7,17 DIONE AND METABOLIZABLE PRECURSORS THEREOF

FIELD OF THE INVENTION

This invention relates to methods and compositions for treating dermatitis.

BACKGROUND

Dermatitis is a chronic inflammatory skin disorder characterized generally by redness, edema, oozing, crusting, scaling, and pruritus. Dermatitis and eczema are often used synonymously and are used synonymously herein, including the claims.

Various types of dermatitis have been classified including contact dermatitis, atopic dermatitis, seborrheic dermatitis (dandruff), nummular dermatitis, pompholyx, psoriasis, generalized exfoliative dermatitis, stasis dermatitis, and localized scratch dermatitis. See, The Merck Manual of Diagnosis and Therapy, $16^{th}$ Edition, Merck & Co. Inc., pp. 2407–2415. As utilized herein, the various types of dermatitis are collectively referenced simply as "dermatitis."

Atopic dermatitis is a chronic inflammatory skin disorder exhibited by individuals with a hereditary predisposition of a lowered cutaneous threshold to pruritus. Atopic dermatitis is often accompanied by allergic rhinitis, hay fever, and asthma. A primary characteristic of atopic dermatitis is extreme itching, leading to repeated scratching which in turn results in the typical lesions of eczema. Infantile eczema occurs predominantly on the cheeks, which may extend to other areas of the body. Eczema occurring on children, adolescents, and adults is found predominantly on the flexural surfaces, especially on the antecubital and popiteal areas, and on the neck, eyelids, wrists, and behind the ears.

In atopic dermatitis, and eczema in general, immunologically mediated leukocyte infiltration (particularly infiltration of mononuclear cells, lymphocytes, neutrophils, and eosinophils) into the skin significantly contributes to the pathogenesis of these diseases. Chronic eczema also is associated with significant hyperproliferation of the epidermis.

Atopic dermatitis and eczema, if sufficiently severe, can lead to death. Less serious, but uncomfortable and often painful symptoms associated with atopic dermatitis include itching, swelling, redness, blisters, crusting, ulceration, pain, scaling, cracking, hair loss, scarring, or oozing of fluid involving the skin, eye or mucosal membranes.

The need to control atopic dermatitis has led to a search for therapeutic agents that are both safe and effective. Corticosteroids, when administered systemically, are effective in this regard but are associated with significant and potentially dangerous side effects. Topically applied corticosteroids have some efficacy in treating these conditions, but are only partially effective in many instances and have their own significant side effects, including atrophy of tissue, formation of telangiectasia, blanching, and a myriad of systemic effects if significantly absorbed. Other agents with partial utility for treating some of the above conditions include psoralen plus ultraviolet A (PUVA), cyclosporin A, ultraviolet A (UVA) and topical Doxepin, for treatment of the associated symptom of pruritis. However, the risk-to-benefit ratios for these agents are unfavorable for most of the conditions described above.

As a result, there is a significant and very long-standing need to identify new agents with favorable benefit to risk ratios that can be applied topically to prevent, suppress or control atopic dermatitis and its associated symptom of (pruritis).

SUMMARY OF THE INVENTION

The invention is directed to the administration of Δ5-androstene-3β-ol-7,17 dione and metabolizable precursors thereof, such as Δ5-androstene-3β-acetoxy-7,17 dione, to treat dermatitis and the associated symptom of pruritis.

DETAILED DESCRIPTION OF THE INVENTION INCLUDING A BEST MODE

Dermatitis can be treated by the administration of Δ5-androstene-3β-ol-7,17 dione and metabolizable precursors thereof, such as Δ5-androstene-3β-acetoxy-7,17 dione, to the skin.

As utilized herein, including the claims, the generic term "dermatitis" collectively refers to the various types of dermatitis, including contact dermatitis, atopic dermatitis, seborrheic dermatitis (dandruff), nummular dermatitis, pompholyx, psoriasis, generalized exfoliative dermatitis, stasis dermatitis, and localized scratch dermatitis.

The Compound

The steroid Δ5-androstene-3β-ol-7,17 dione is a derivative of dehydroepiandrosterone (DHEA) which does not appreciably stimulate, increase or otherwise enhance the production of sex hormones. The steroid is commercially available from a number of sources including Steraloids, Inc. of Wilton, New Hampshire. A number of procedures are available for synthesizing Δ5-androstene-3β-ol-7,17 dione from DHEA, with one such procedure described in U.S. Pat. No. 5,296,481.

Precursors of Δ5-androstene-3β-ol-7,17 dione may also be usefully employed in the treatment of dermatitis. Such precursors are readily metabolized in vivo to the active Δ5-androstene-3β-ol-7,17 dione. One example of such a metabolizable precursor is the commercially available Δ5-androstene-3β-acetyl-7,17 dione. The 3β-acetyl group is hydrolyzed in vivo by esterases located in the blood and various tissue, including the skin, to produce the active Δ5-androstene-3β-ol-7,17 dione, and is believed to be less susceptible to oxidation during the manufacturing process than the hydroxy group found on the active Δ5-androstene-3β-ol-7,17 dione. The steroid is commercially available from Humanetics Corporation of Chanhassen, Minnesota under the trademark "7-KETO."

Other metabolizable precursors include Δ5-androstene-3β, 17β-diol-7-one, Δ5-androstene-3β, 7Δ-diol-17-one, Δ5-androstene-3β, 7β-diol-17-one and the corresponding acetyl esters of these steroids.

Administration

The steroid can be conveniently administered by incorporating the steroid into a lipophilic carrier to form a cream, lotion, ointment, gel, pomade, or balm (hereinafter collectively referenced as composition) and topically applying the composition to the affected area.

The composition can include from about 0.2 to 20-wt % steroid, preferably about 0.5 to 10-wt %, steroid. A concentration of less than about 0.2-wt % steroid tends to require the application of an uncomfortably large amount of the composition to achieve the desired effect while a concentration of greater than about 20-wt % steroid tends to increase the cost of the composition without a corresponding increase in the diminishment or control of dermatitis.

The composition can contain those adjuvants or additives which are commonly included in such compositions, such as hydrophilic or lipophilic gelling agents, preservatives, antioxidants, solvents, fragrances, fillers, screening agents, and colorants. The amounts of these various adjuvants or additives are those conventionally used in the cosmetics and dermatological fields, which are commonly from about 0.01 to about 20-wt % of the composition.

The composition can be beneficially employed by topically applying the steroid to the skin on a daily basis, such as after bathing or just prior to bedtime.

I claim:

1. A method of treating dermatitis comprising administering an effective amount of a composition consisting essentially of a compound selected from Δ5-androstene-3β-ol-7,17 dione, Δ5-androstene-3β,17β-diol-7-one, Δ5-androstene-3β,7α-diol-17-one, Δ5-androstene-3β,7βp-diol-17-one and corresponding acetyl esters thereof to skin in need of such treatment.

2. The method of claim 1 wherein the dermatitis is contact dermatitis.

3. The method of claim 1 wherein the dermatitis is atopic dermatitis.

4. The method of claim 1 wherein the dermatitis is seborrheic dermatitis.

5. The method of claim 1 wherein the dermatitis is psoriasis.

6. The method of claim 1 wherein the compound is provided in an acceptable carrier as a topical cream, lotion, ointment, gel, pomade, or balm.

7. The method of claim 1 wherein the composition is administered topically.

8. The method of claim 1 wherein the compound is Δ5-androstene-3β-acetyl-7,17 dione.

9. The method of claim 7 wherein the compound is Δ5-androstene-3β-acetyl-7,17 dione.

10. The method of claim 1 wherein the compound is administered at least once a day.

11. The method of claim 8 wherein the compound is administered at least once a day.

12. The method of claim 1 wherein the skin is human skin.

13. The method of claim 7 wherein the skin is human skin.

14. The method of claim 8 wherein the skin is human skin.

15. The method of claim 9 wherein the skin is human skin.

* * * * *

UNITED STATES PATENT AND TRADEMARK OFFICE
CERTIFICATE OF CORRECTION

PATENT NO. : 6,465,446 B1
DATED : October 15, 2002
INVENTOR(S) : Dykstra

It is certified that error appears in the above-identified patent and that said Letters Patent is hereby corrected as shown below:

Column 2,
Line 49, replace "Δ5-androstene-3β, 7Δ-diol" with -- Δ5-androstene-3β, 7α-diol --

Column 3,
Line 15, replace "Δ5-androstene-3β, 7β p-" with -- Δ5-androstene-3β, 7β- --

Signed and Sealed this

Eighteenth Day of February, 2003

JAMES E. ROGAN
*Director of the United States Patent and Trademark Office*